US010578607B2

(12) United States Patent
Wu et al.

(10) Patent No.: US 10,578,607 B2
(45) Date of Patent: Mar. 3, 2020

(54) METHOD OF SCREENING, ISOLATING, AND PURIFYING RARE CELLS

(71) Applicants: Min-Hsien Wu, Kaohsiung (TW);
Wen-Pin Chou, Taipei (TW);
Tzu-Keng Chiu, New Taipei (TW);
Po-Yu Chu, Nantou County (TW)

(72) Inventors: Min-Hsien Wu, Kaohsiung (TW);
Wen-Pin Chou, Taipei (TW);
Tzu-Keng Chiu, New Taipei (TW);
Po-Yu Chu, Nantou County (TW)

(73) Assignee: Chang Gung University, Taoyuan (TW)

( * ) Notice: Subject to any disclaimer, the term of this patent is extended or adjusted under 35 U.S.C. 154(b) by 93 days.

(21) Appl. No.: 15/817,431

(22) Filed: Nov. 20, 2017

(65) Prior Publication Data

US 2019/0154657 A1    May 23, 2019

(51) Int. Cl.
*G01N 33/49*  (2006.01)
*C12N 5/09*   (2010.01)
*G01N 27/327* (2006.01)
*G01N 33/574* (2006.01)
(Continued)

(52) U.S. Cl.
CPC ......... *G01N 33/491* (2013.01); *C12N 5/0693* (2013.01); *C12N 13/00* (2013.01); *G01N 27/327* (2013.01); *G01N 27/44756* (2013.01); *G01N 33/574* (2013.01)

(58) Field of Classification Search
CPC ........... G01N 33/491; G01N 27/44756; G01N 27/327; G01N 33/574; C12N 13/00; C12N 5/0693
See application file for complete search history.

(56) References Cited

U.S. PATENT DOCUMENTS

2017/0184545 A1*  6/2017  Azpiroz .......... G01N 27/44791

FOREIGN PATENT DOCUMENTS

TW            201018905 A       5/2010

OTHER PUBLICATIONS

Song-Bin Huang, Jian Chen, Junbo Wang, Chih-Liang Yang and Min-Hsien Wu, A New Optically-Induced Dielectrophoretic (ODEP) Force-Based Scheme for Effective Cell Sorting, International Journal Electrochemical Science, Dec. 2, 2012, pp. 12656-12667 (12 pages), vol. 7 2012, www.electrochemsci.org.

(Continued)

*Primary Examiner* — Tony Ko (57) ABSTRACT

A method of screening, isolating and purifying rare cells includes obtaining cell groups with rare cells from a sample, removing cells not to be screened from the cell groups, and drawing the remaining cells as a cell suspension sample. An introduction device is activated to load the cell suspension sample onto an optically-induced dielectrophoresis chip including a cell isolation zone having a division arrangement wherein at least one optical pattern is configured on the cell isolation zone for screening, isolating and purifying the rare cells. The at least one optical pattern is configured to migrate, rotate or both. The at least one optical pattern is activated to attract the rare cells into a collection tank on the chip, and a liquid drawing device is activated to draw the rare cells out of the collection tank, thereby obtaining purified rare cells from the sample.

11 Claims, 5 Drawing Sheets

(51) Int. Cl.
*G01N 27/447* (2006.01)
*C12N 13/00* (2006.01)

(56) References Cited

OTHER PUBLICATIONS

Wen-Pin Chou, Hung-Ming Wang, Jyun-Huan Chang, Tzu-Keng Chiu, Chia-Hsun Hsieh, Chia-Jung Liao and Min-Hsien Wu, The utilization of optically-induced-dielectrophoresis (ODEP)-basedvirtual cell filters in a microfluidic system for continuous isolation andpurification of circulating tumour cells (CTCs) based on their sizecharacteristics, Sensors and Actuators B: Chemical, Oct. 18, 2016 (available online), pp. 245-254 (10 pages), vol. 241 (2017), www.elsevier.com/locate/snb.

Tzu-Keng Chiu, Wen-Pin Chou, Song-Bin Huang, Hung-Ming Wang, Yung-Chang Lin, Chia-Hsun Hsieh & Min-Hsien Wu, Application of optically-induced-dielectrophoresis in microfluidic system for purification of circulating tumour cells for gene expression analysis—Cancer cell line model, Scientific Reports, Sep. 2016 (published), pp. 1-14, Scientific Reports 6 Article No. 32851 (2016), https://www.nature.com/articles/srep32851.

\* cited by examiner

| | |
|---|---|
| 🍇 | CTCs cluster |
| ⇐ | flow of fluid in the cells to be sifted |
| ← | direction of migration of optical pattern |
| ← | direction of rotation of optical pattern |
| ↻ | rotation of optical pattern |

FIG.4

METHOD OF SCREENING, ISOLATING, AND PURIFYING RARE CELLS

BACKGROUND OF THE INVENTION

1. Field of the Invention

The invention relates to methods of purifying rare cells and more particularly to a method of screening, isolating and purifying rare cells by using dynamic optical patterns and optically-induced dielectrophoresis, in which cells are screened by the migration and rotation of at least one dynamic optical pattern and forces in different directions, so that the efficiency and the resolution can be increased greatly.

2. Description of Related Art

Currently, cancer treatment has made a great progress, but the treatments are still limited by extent of seriousness, by the fast speed of cancer metastasis and development of drug resistance. Thus, a complete cure for cancer is not yet possible. Clinical diagnosis of cancer relies on biopsy and biomarker detection. Nevertheless, these methods do not reveal the current conditions of tumors. Furthermore, sampling is a complicated procedure, which may prolong rehabilitation time of a patient after surgery.

CTCs (circulating tumor cells) were found in blood of a cancer patient in 1869. Thereafter, many documents proving that CTCs are associated with cancer metastasis by animal experiments and clinical trials were disclosed. In turn, this lead to the development of techniques of detection and separation of CTCs. But some recent documents disclosed that cancer metastasis is not caused by single CTCs but by CTCs clusters. Moreover, the metastatic cancer is in the form of polyclone. This not only proves cancer metastasis tends to be caused by CTC clusters, but also suggests that a gene form of the CTCs clusters could reflect a more real condition of the cancer progression.

CTCs identification is made possible due to characteristics of its surface antigens such as EpCAM (Epithelial Cell Adhesion Molecule), CKs (cytokeratins) and Vimentin. An antibody with a florescent marker is specific to the aforementioned antigens. Thus, separation and purification of CTCs can be done by a specific catching technique such as immunomagnetic beads. In addition, for increasing the identification rate, most catching techniques employ a negative sift on the specific antigen CD45 inherent to the white blood cells and a positive sift on Nucleus. Cells are identified as CTCs only when antigens of CTCs and cores thereof are positive and antigens of white blood cells are negative. However, such identification is only feasible when surface antigens of cells are stable. Certain documents doubt employing EpCAM as CTCs identification antigens and their arguments are as follows:

1. EpCAM does not stably exist on surfaces of CTCs, especially CTCs of EMT (Epithelial-to-Mesenchymal Transition) and EpCAM antigens on its surfaces are greatly decreased.

2. CTCs may absorb a great amount of platelets on its surfaces for evading immunity identification. Also, antigens on surfaces of cells may change as surrounding conditions change. Thus, some CTCs may be not screened when an immunity technique is employed for screening. And in turn, it may cause errors in a subsequent gene analysis and adversely affect clinical applications.

Physical technique for separation is employed due to the limitation of the immunity technique. Different from CTCs, CTCs clusters include two or more cancer cells. Thus, cell size can be employed for CTCs clusters isolation and purification. For example, Microfilter and Inertial Microfluidics are designed based on this principle. While these techniques achieve the purpose of CTCs clusters isolation, it is impossible to avoid cells clogged with small filter pores. Thus, a previous collection rate may be different from a subsequent one. Further, for the purpose high throughput, separation is required to be done in a high flow rate. However, the shear force caused by the high flow rate may destroy the CTCs cluster. And in turn, it will adversely affect the collection of CTCs clusters.

A number of patents disclose employing magnetic beads for CTCs automatic separation and culture. However, the magnetic beads cannot separate the CTCs clusters only. Therefore, isolation precision is poor and technologies are out of date. Some patents disclose employing optically-induced dielectrophoresis for micro particles separation. However, the optically-induced dielectrophoresis does not have the capabilities of migration and rotation and is not applied to CTCs clusters isolation.

Thus, the need for improvement still exists.

SUMMARY OF THE INVENTION

It is therefore one object of the invention to provide a method of screening, isolating and purifying rare cells by using dynamic optical patterns and applying optically-induced dielectrophoresis in which migration and rotation of at least one optical pattern is employed to screen, isolate and purify rare cells in a sample.

Technological characteristics of the invention involve eliminating cells not to be screened from a sample, applying optically-induced dielectrophoresis on the remaining cells to screen rare cells, and using migration or rotation of the optical patterns to greatly increase separation rate, collection rate, and precision.

One aspect of the invention to provide a method of screening, isolating, and purifying rare cells by using a dynamic optical patterns and applying optically-induced dielectrophoresis includes the steps of obtaining cell groups with rare cells in from a sample, and then removing cells not to be screened from the cell groups to leave remaining cells by the biological or physical method, and drawing the remaining cells as a cell suspension sample, activating an introduction device to load the cell suspension sample onto an optically-induced dielectrophoresis chip, including a cell isolation zone having a division arrangement, wherein at least one projected optical pattern at the cell isolation zones. Combined with an optically-induced dielectrophoresis force, the rare cells are isolated and purified from the cell suspension sample. The illuminated optical patterns are able to migrate, rotate or both, and the rare cells are selectively attracted by the optical patterns due to ODEP force, entering the collection tank of the chip. Then, a drawing device is used to draw the rare cells out of the collection tank.

Preferably, the cells not to be screened are red blood cells.

Preferably, the cell suspension sample includes white blood cells, CTCs, CTC clusters and all immature blood cells.

Preferably, the rare cells are CTCs clusters.

Preferably, the biological method employs reagents for antibody to catch red blood cells.

Preferably, the physical method is Ficoll reagent, red blood cells breakage reagent, or sieve device.

The invention has the following advantages and benefits in comparison with the conventional art:

1. The working principle of this invention includes removing cells not to be screened and destroying CTCs clusters based on the cell size difference, and then by applying optical patterns with capabilities of migration and rotation, the rare cells can be screened, isolated, and purified. During the operation, it is unnecessary to adjust the optical patterns, so a long-term, stable, and efficient rare cells isolation platform is provided.

2. CTCs clusters can be collected by a purification platform for higher-purity cell isolation, avoiding the interference caused by co-existing blood cells. After removing cells not to be screened and loading the remaining cells onto an optically-induced dielectrophoresis chip, the three forces, including flow of the sample fluid and migration and rotation of optical patterns, may isolate CTCs clusters from the remaining cells, thereby achieving the purpose of automatic purification. According to the amount of CTCs clusters collected by this platform, the cancer progress of a patient, prognosis, and the possibility of metastasis could be assessed. Further, in cooperation with gene identification techniques such as qPCR and NGS, it is possible to predict the development of drug resistance of cancer cells, thereby enabling a physician to evaluate the performance of the cancer treatment and change the treatment strategy when needed.

3. By taking advantage of the optically-induced dielectrophoresis chip and dynamic optical patterns, it can avoid cells clogged with small filter pores and the shear force caused by the high flow rate when the fluid passes through the filter, thereby increasing the collection rate of the purified CTCs clusters, decreasing the adverse affection of the system to the cells, improving reliability of a subsequent gene analysis.

4. After removing the cells not to be screened in a pre-process, CTCs clusters can be isolated by an optically-induced dielectrophoresis and dynamic optical patterns, without a cell-marking process. In other words, the invention provides a label-free automatic platform for CTCs clusters isolation. In comparison with other Immunolabeling technologies, the operation of the invention is relatively easy and is not adversely affected by the type of antibody. Further, a low cell collection rate resulting from cells clogging phenomenon due to long time operation is not possible.

5. An optically-induced dielectrophoresis chip is different from the physical filter. A simple motion of optical patterns provides two different kinds of force, i.e., migration and rotation, to a cell suspension sample. Further, if a micro injection pump is used, the flow of sample fluid could be applied to the cell suspension sample as the third force. This increases isolation precision of CTCs clusters of the platform. Also, isolation efficiency of this invention is greatly increased over the efficiency of the platform only providing two different kinds of force by optical patterns.

6. The target of collection is CTCs clusters. The range of the target of collection is wide since there is no definition of the number of cells in a CTCs cluster. The platform of the invention uses several equal distance optical patterns and the optical patterns can be either a repetitive pattern or a non-repeat pattern, thereby greatly increasing the collection rate of the CTCs clusters and the accuracy of a subsequent analysis. The results can be used to create an individual clinical database for each cancer patient, thereby providing an improved cancer treatment for each cancer patient and the personalized treatment. Also, the culture of CTCs clusters is much easier to succeed and contributes greatly to the establishment of cell lines of clinical cancer cells. The stable cell lines can be used for research. Further, a medicine manufacturing company can employ the stable cell lines for medicine tests, and analysis of gene, protein and surface antigen, thereby contributing greatly to the advancement of technologies.

The above and other objects, features and advantages of the invention will become apparent from the following detailed description taken with the accompanying drawings.

DETAILED DESCRIPTION OF THE INVENTION

Referring to FIGS. 1 to 4, a method of screening, isolating and purifying rare cells by using dynamic optical patterns and applying optically-induced dielectrophoresis in accordance with the invention is illustrated in a flow chart. The method comprises the following steps as discussed in detail below.

Figure 1:
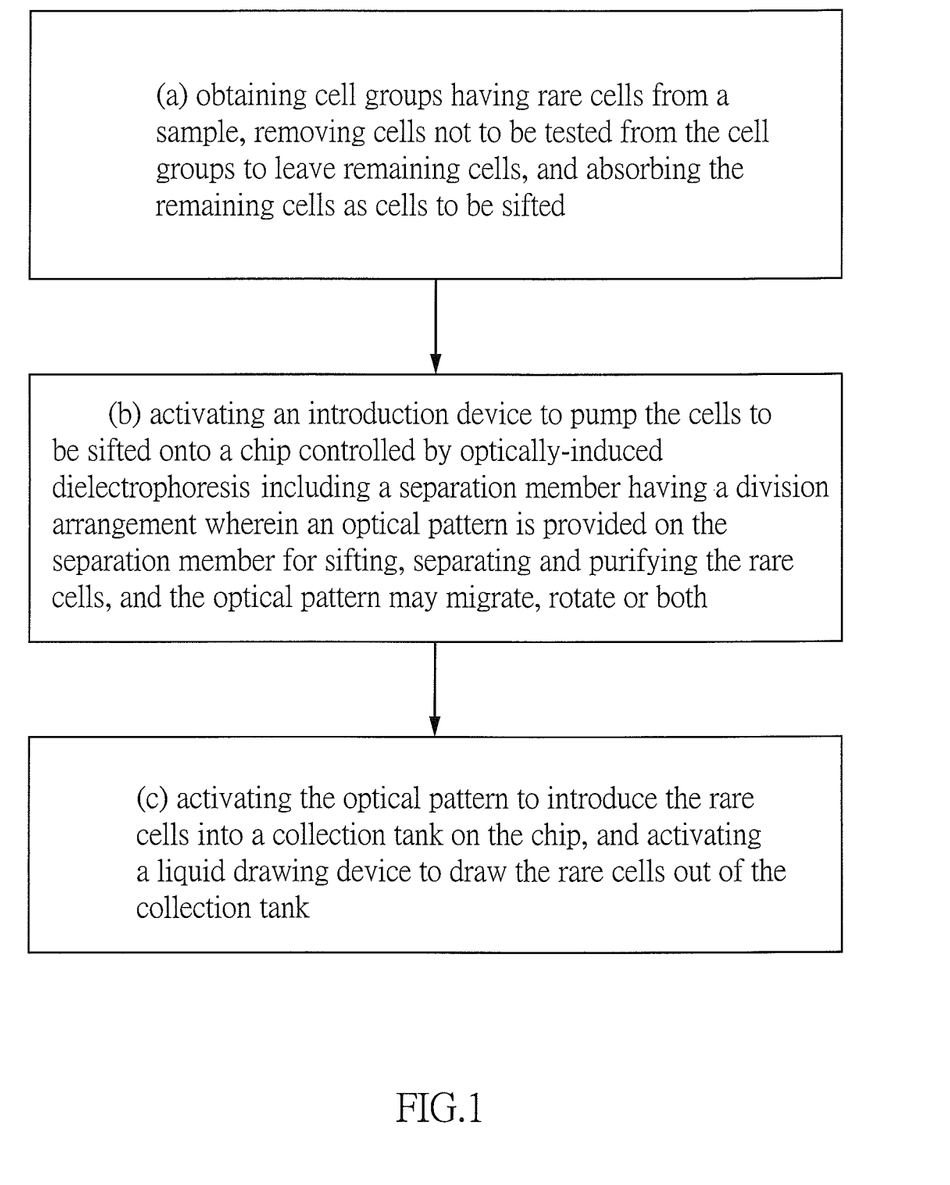
FIG. 1 is a flow chart of a method of screening, separating and purifying rare cells by using dynamic optical pattern and optically-induced dielectrophoresis according to the invention.

(a) Blood having at least one CTCs cluster 20 is obtained from a sample. Existing Ficoll reagent is used to separate the sample from the red blood cells to obtain cell suspension sample 10 having white blood cells and the CTCs clusters 20. In the cell suspension sample 10, weight percentage of the CTCs clusters 20 is about equal to that of the white blood cells. Thus, the white blood cells are separated from the cell suspension sample 10 for a subsequent cell analysis.

(b) An introduction device (e.g., micropipette) 12 is used to load the cell suspension sample 10 onto an optically-induced dielectrophoresis chip 14 by physical drive. The optically-induced dielectrophoresis chip 14 includes a cell isolation zone 1441 having a division arrangement. A plurality of optical patterns 16 is configured on the cell isolation zone 1441 to form a spaced array 162. Each optical pattern 16 can appear or disappear in a predetermined time. Combining the migration and rotation of optical patterns and an optically-induced dielectrophoresis force, the CTCs clusters 20 screening, isolation and purification from the cell suspension sample 10 can be done simultaneously. Each optical pattern 16 migrates independently and can be either a repetitive pattern or a non-repeat pattern.

(c) The CTCs clusters 20 are attracted into a collection tank 1413 by the optical patterns 16 in the optically-induced dielectrophoresis chip 14. Next, a liquid drawing device 18 (e.g., micropipette) is used to draw the CTCs clusters 20 out of the collection tank 1413. The physical drive is a pressurized, electromagnetic or optical drive. The pressurized drive is done by an injection pump or a worm-drive pump. The electromagnetic drive is done by an electromagnetic pump. The optical drive is done by photo-induced electrophoresis force.

The sample is blood. The Ficoll reagent is Ficoll-Paque plus whose main ingredients are macromolecular sucrose polymers and a sodium solution. A density gradient is formed by Ficoll reagent in specific centrifuge conditions, so that the blood cells could be separated according to different cell density.

Figure 2:
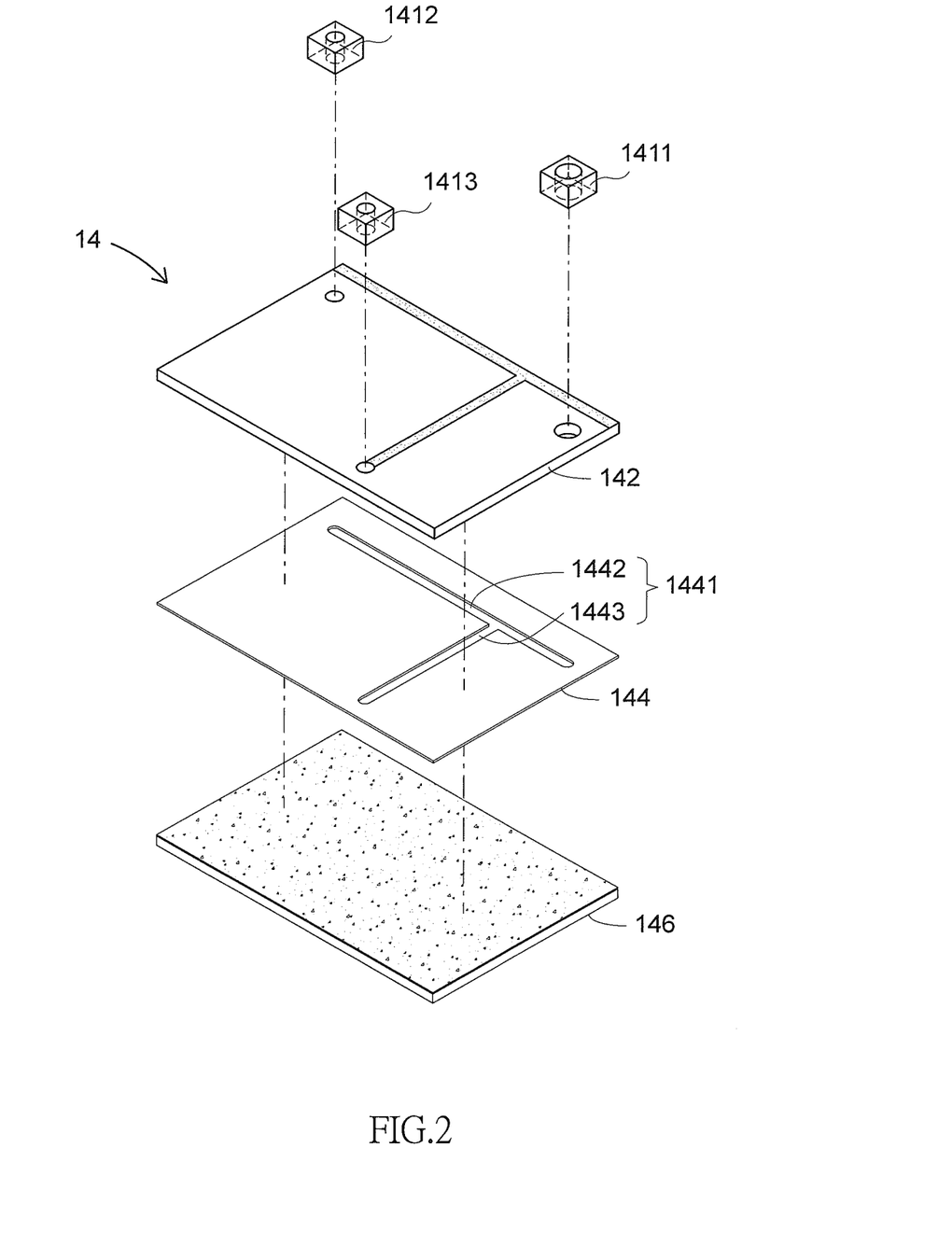
FIG. 2 is an exploded view of an optically-induced dielectrophoresis chip.
Figure 3:
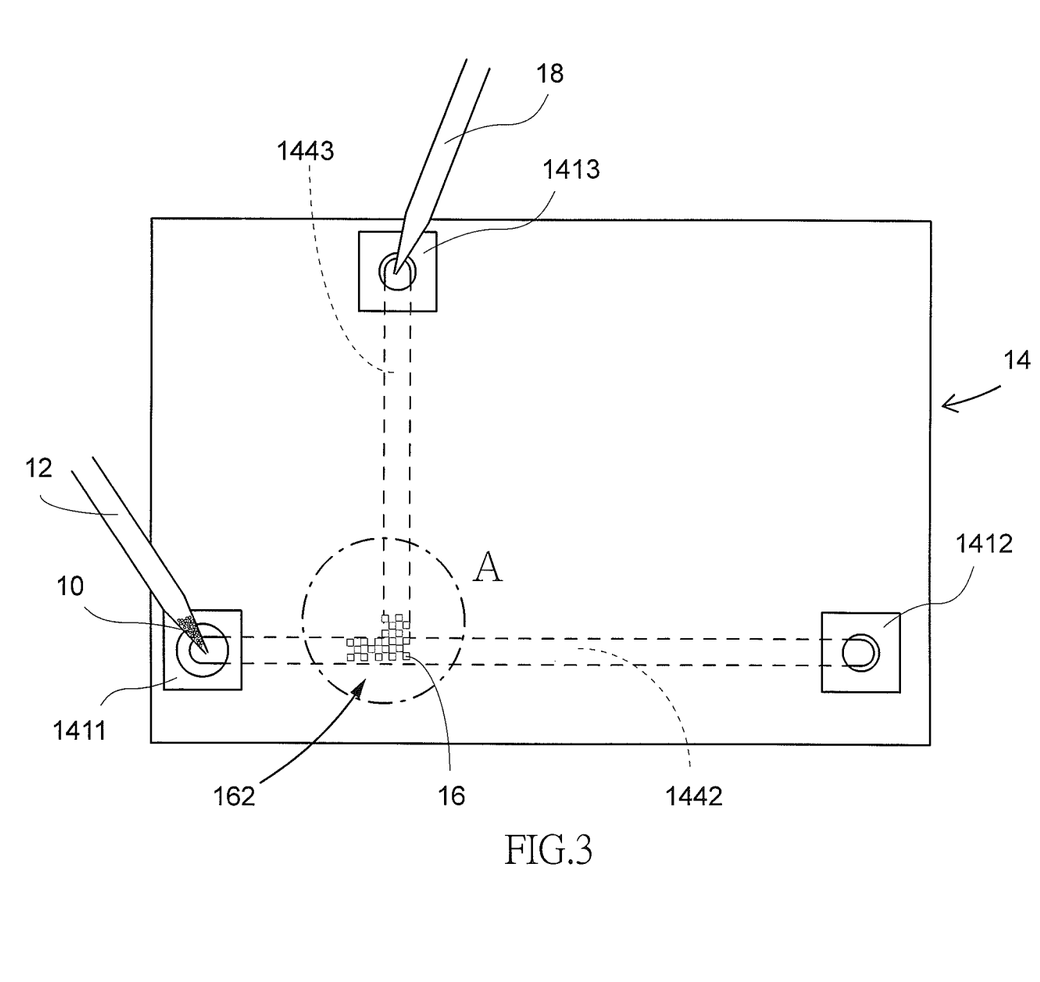
FIG. 3 schematically depicts an operation of an optically-induced dielectrophoresis chip.
Figure 3A:
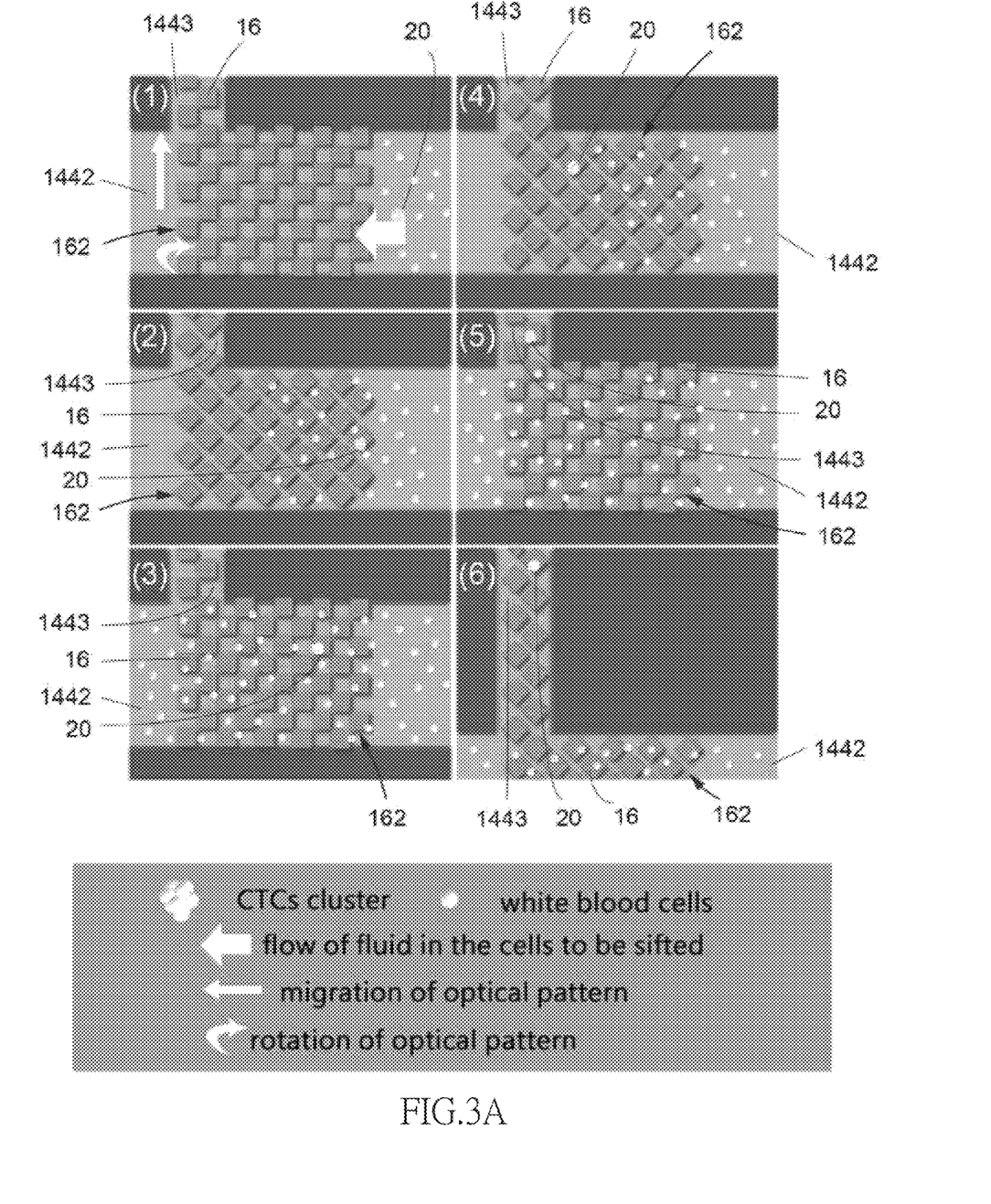
FIG. 3A schematically depicts migration and rotation of a plurality of optical patterns.

As shown in FIGS. 2 to 3A, the optically-induced dielectrophoresis chip 14 of the invention is a chip having optical and electric characteristics and isolation, purification conducted by means of electric potential difference. The optically-induced dielectrophoresis chip 14 includes, from top to bottom, a first layer having an injection tank 1411, a waste removal tank 1412 and a collection tank 1413 all made of polydimethylsiloxane (PDMS); a second layer having an electrode channel layer 142 made of indium tin oxide (ITO); and a third layer having a channel layer 144 made of biocompatible double sided tape. The channel layer 144 is provided with a cell isolation zone 1441 having a main channel 1442 and a side channel 1443 for preventing white blood cells from polluting the CTCs clusters 20. The injection tank 1411 and the waste removal tank 1412 are set above two ends of the main channel 1442 respectively. The introduction device 12 may load the cell suspension sample 10 to flow from the injection tank 1411 to the main channel 1442. The waste removal tank 1412 can collect white blood cells and excessive fluid. The collection tank 1413 is provided above the end of the side channel 1443 for collecting the CTCs clusters 20. The injection tank 1411, the waste removal tank 1412 and the collection tank 1413 are provided through the electrode channel layer 142 and communicate with the cell isolation zone 1441. A base layer 146 is coated with amorphous silicon on its top surface and formed of ITO (indium tin oxide). An optical pattern 16 is provided at a joining portion of the main channel 1442 and the side channel 1443. Each optical pattern 16 can migrate and rotate to separate the CTCs clusters 20 from the white blood cells and further attract the CTCs clusters 20 into the collection tank 1413 at the end of the side channel 1443.

FIG. 3 schematically depicts an operation of the optically-induced dielectrophoresis chip 14 and FIG. 3A schematically depicts migration and rotation of a plurality of optical patterns 16 respectively. Operations of the invention are discussed below. The introduction device 12 (e.g., micropipette) is used to load the cell suspension sample 10 onto the optically-induced dielectrophoresis chip 14. The optically-induced dielectrophoresis chip 14 has the cell isolation zone 1441 and a plurality of the optical patterns 16 are configured on the cell isolation zone 1441. The cell suspension sample 10 flows through the array 162 which includes a plurality of spaced optical patterns 16. Each optical pattern 16 is a single motion unit and capable to migrate or rotate independently. The CTCs clusters 20 in the cell suspension sample 10 move toward the side channel 1443 due to the flow of the cell suspension sample 10, the forces caused by migration of the optical patterns 16 and by the rotation of the optical patterns 16. When the movement of the CTCs clusters 20 is affected by the optical patterns 16, the white blood cells in the cell suspension sample 10 are not affected by the optically-induced dielectrophoresis force and move toward the waste removal tank 1412 with the flow of cell suspension sample 10. The CTCs clusters 20 move toward the side channel 1443 due to the flow of the culture solution or of the cell suspension sample 10 fluid. After the CTCs clusters 20 arriving at the entrance of the side channel 1443, the CTCs clusters 20 will be attracted to the end of the side channel 1443 due to the force applied by the optical patterns 16. The CTCs clusters 20 in the side channel 1443 are not affected by the flow of the cell suspension sample 10, so the CTCs clusters 20 will only be affected by the migration and rotation of the optical patterns 16, moving toward the collection tank 1413 at the end of the side channel 1443. The liquid drawing device 18 (e.g., micropipette) is used to draw the CTCs clusters 20 out of the collection tank 1413. As such, the CTCs clusters 20 are obtained from the optically-induced dielectrophoresis chip 14.

Figure 4:
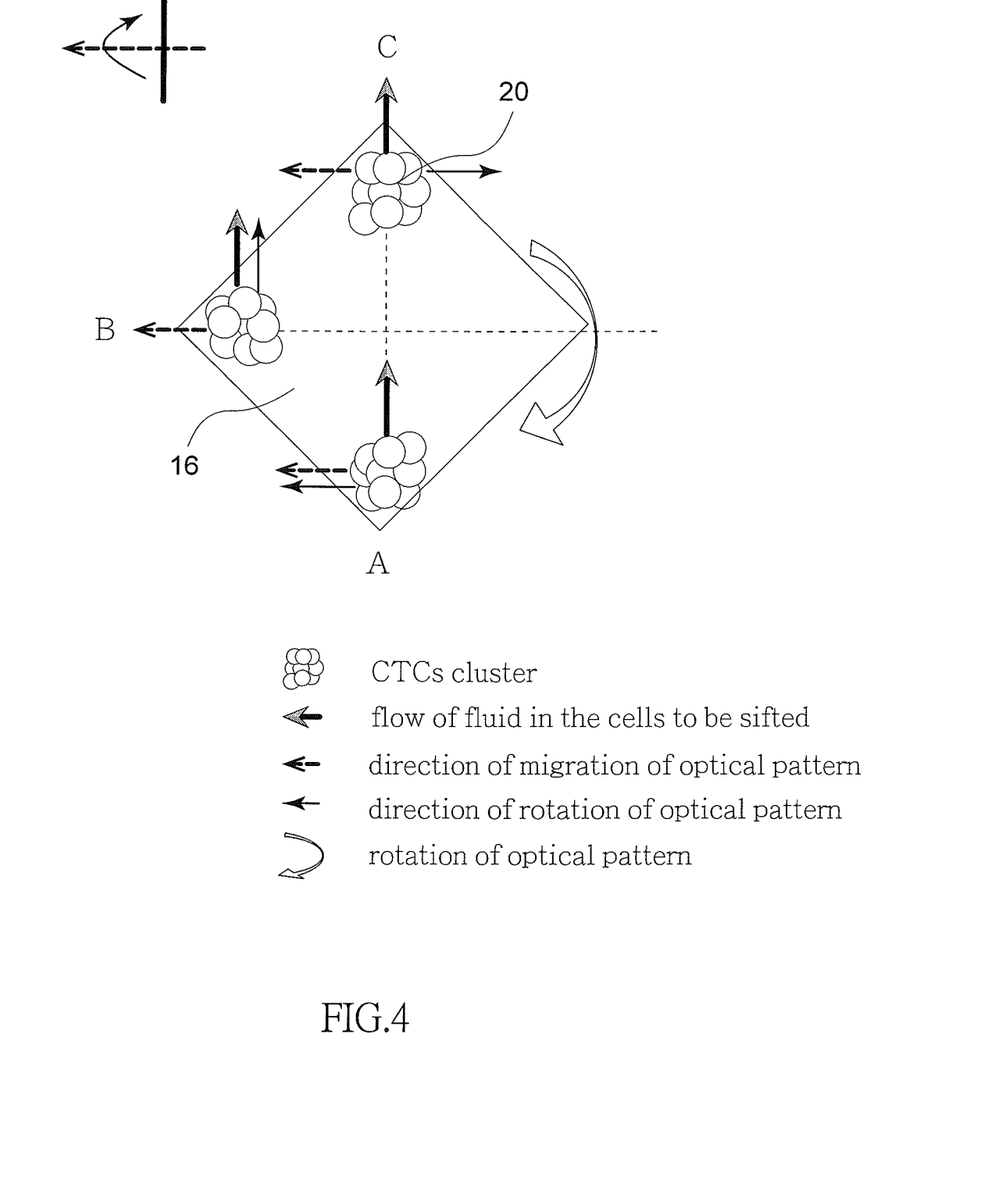
FIG. 4 schematically depicts directions of different forces applied to a single optical pattern.

Referring to FIG. 4 in conjunction with FIGS. 3 and 3A, FIG. 4 schematically depicts directions of different forces applied on a single optical pattern 16. As shown in FIG. 4, the CTCs clusters 20 on the optically-induced dielectrophoresis chip 14 are affected by forces from three different directions, i.e., force from the flow of the cell suspension sample 10, force caused by the migration of the optical patterns 16 and the rotation of the optical patterns 16. Direction of the flow of the cell suspension sample 10 is perpendicular to that of the rotation of the optical pattern 16. Force applied by the migration of the optical pattern 16 changes its direction when the CTCs clusters 20 move from one place to another place. For example, in the position labeled A, force applied by the rotation of the optical pattern 16 is parallel to force applied by the migration of the optical pattern 16. Thus, these two forces are added to create a greater force. And in turn, white blood cells are thrown out of the optical pattern 16 due to less application of optically-induced dielectrophoresis. As a result, only CTCs clusters 20 affected by a strong force are left. Likewise, in the position labeled B, force applied by the rotation of the optical pattern 16 is parallel to force applied by the flow of the cell suspension sample 10. As a result, the CTCs clusters 20 move toward upstream of the channel. Also likewise, in the position labeled C, force applied by the migration of the optical pattern 16 is opposite to force applied by the rotation of the optical patterns 16. These forces cancel each other. As a result, the CTCs clusters 20 move toward a same direction as that of force applied by the flow of the cell suspension sample 10.

While the invention has been described in terms of preferred embodiments, those skilled in the art will recognize that the invention can be practiced with modifications within the spirit and scope of the appended claims.

What is claimed is:

1. A method of screening, isolating and purifying rare cells by using dynamic optical patterns and optically-induced dielectrophoresis comprising the steps of:
   (a) obtaining cell groups with rare cells in from a sample, removing cells not to be screened from the cell groups, and then drawing the remaining cells as cell suspension sample;
   (b) activating an introduction device to load the cell suspension sample onto an optically-induced dielectrophoresis chip including a cell isolation zone having a division arrangement wherein at least one optical pattern is configured on the cell isolation zone for screening, isolating and purifying the rare cells, and the at least one optical pattern is configured to migrate, rotate or both; and
   (c) activating the screening, isolating and purifying by the optical patterns, wherein the rare cells are attracted into a collection tank on the optically-induced dielectrophoresis chip, thereby activating a liquid drawing device to draw the rare cells out of the collection tank.

2. The method of claim 1, wherein the at least one optical pattern is more than one, wherein the plurality of the optical patterns are configured to form a spaced array, and wherein each optical pattern is a single motion unit.

3. The method of claim 2, wherein each optical pattern is either a repetitive pattern or a non-repeat pattern.

4. The method of claim 1, wherein each of the at least one optical pattern is configured to freely migrate and appear or disappear in a predetermined time.

5. The method of claim 2, wherein each of the at least one optical pattern is configured to freely migrate and appear or disappear in a predetermined time.

6. The method of claim 1, wherein in step (b) after activating an introduction device to load the cell suspension sample onto a optically-induced dielectrophoresis chip, the cell suspension sample are affected by flow of itself, the migration of the at least one optical pattern, and the rotation of the at least one optical pattern, and the flow of the cell suspension sample being perpendicular to the migration direction of the at least one optical pattern.

7. The method of claim 1, wherein in step (a) the removal of the cells not to be screened from the cell groups is done by either a biological technique or a physical technique.

8. The method of claim 1, wherein both the introduction device in step (b) and the liquid drawing device in step (c) are activated by a physical drive which is a pressurized, electromagnetic or optical drive.

9. The method of claim 1, wherein the purified rare cells obtained in step (c) are contributed to cell lines establishment of clinical cancer cell for research, enable a medicine manufacturing company to employ the cell lines for medicine tests and analysis of gene, protein and surface antigen, use the results to create an individual clinical database for each cancer patient, and provide an improved cancer treatment for respective cancer patients.

10. The method of claim 1, wherein the rare cells are CTCs clusters.

11. The method of claim 1, wherein the sample is blood.

* * * * *